United States Patent [19]

Coussediere et al.

[11] 4,064,339
[45] Dec. 20, 1977

[54] ANTIBIOTIC AMINOGLYCOSIDES, PROCESSES OF PREPARATION AND PHARMACEUTICAL COMPOSITIONS

[75] Inventors: Daniel Coussediére, Villejuif; Jean-Claude Gasc, Bondy, both of France

[73] Assignee: Roussel UCLAF, Paris, France

[21] Appl. No.: 557,310

[22] Filed: Mar. 11, 1975

[30] Foreign Application Priority Data

Mar. 12, 1974 France ................. 74.08316

[51] Int. Cl.$^2$ ............... C07H 15/22; A61K 31/71
[52] U.S. Cl. .................... 536/17; 424/180; 536/4; 536/18; 536/53; 536/122
[58] Field of Search ........ 260/210 AB, 210 K, 210 R; 536/17, 4, 53

[56] References Cited

U.S. PATENT DOCUMENTS

| | | | |
|---|---|---|---|
| 3,350,387 | 10/1967 | Vanderhaeghe | 260/210 R |
| 3,925,353 | 12/1975 | Umezawa et al. | 536/17 |
| 3,925,354 | 12/1975 | Umezawa et al. | 536/17 |
| 3,959,255 | 5/1976 | Chazan et al. | 536/17 |

OTHER PUBLICATIONS

Kojima et al., "The Jour. of Antibiotics" vol. XXVI, No. 12, pp. 784–785, 1973.

*Primary Examiner*—Johnnie R. Brown
*Attorney, Agent, or Firm*—Bacon & Thomas

[57] ABSTRACT

There are disclosed pharmaceutically-active aminoglycosides comprising 4-O-(2',6'-diamino 2',6'-didesoxy α,D-glucopyrannosyl) 6-O-(3''-amino 3'',4'',6''-tridesoxy α, D-xylohexopyrannosyl) 2-desoxy streptamine of the formula:

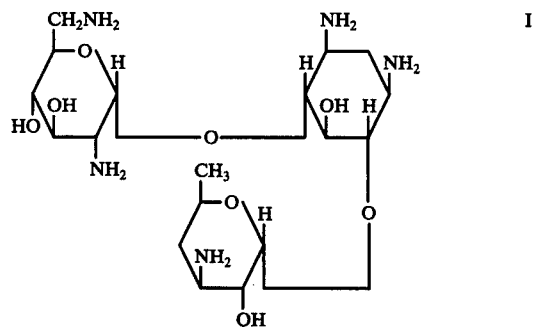

and the addition salts thereof with mineral acids or organic acids. Also disclosed are methods for preparation of the novel products as well as certain novel intermediate products. There are also disclosed pharmaceutical compositions in which the novel products are the active agents as well as methods for use of compositions as antibiotic agents.

3 Claims, No Drawings

ANTIBIOTIC AMINOGLYCOSIDES, PROCESSES OF PREPARATION AND PHARMACEUTICAL COMPOSITIONS

The present invention concerns new derivatives of Aminoglycosides and their process of preparation. These compounds are pharmaceutically active as antibiotics. Thus, the main object of the present invention is new derivatives of Aminoglycosides, namely,

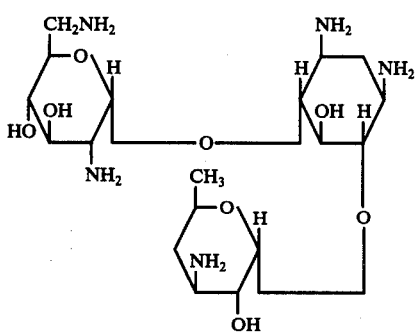

I as well as addition salts thereof with mineral or organic acids. These salts may be obtained by the complete or partial neutralization of the five amino functional groups.

Such addition salts include, for example, chlorhydrate, bromhydrate, nitrate, sulfate, phosphate, acetate, formate, benzoate, maleate, fumarate, succinate, tartrate, citrate, oxalate, benzylate, glyoxylate, aspartate, alkylsulfonate such as methane sulfonate, arylsulfonate such as p-toluene sulfonate, or the like which are formed by using the corresponding acid.

Another object of the invention is the provision of pharmaceutical compositions particularly antibiotic compositions which include, as the active principle, the product of formula I or one of its therapeutically compatible salts. The aforementioned products possess very interesting antibiotic activities on the bacteria gram (+) such as Staphylococci, Streptococci and notably penicillin resistant Staphylococci as well as on the bacteria gram (−), and notably coliform bacteria. Thus, they are useful in the treatment of humans and animals which are affected by these bacteria.

These properties render the product of formula I as well as its therapeutically compatible salts suitable for use as medication notably in the treatment of staphylococci such as those which are responsible for blood poisoning, skin diseases and infections on the face, pyodermites, septic and running sores, anthrax or carbuncles, phlegmons, erysipelas and the like. Also, acute staphylococci which arise in both the early stages and after influenza, bronchopneumonia, and other infections of the lung including lung congestion can be treated by the products of this invention. Further, the products of the invention can be used against collibacilloses.

These products can be used parenterally, orally, rectally or locally by topical application on the skin or mucous membrane. They can be given in the form of injectable solutions or suspensions, sterile powders for improvised injectable preparations, tablets, capsules, syrups, suppositories, creams, pommades and aerosol preparations. These pharmaceutical forms are prepared according to the standard processes. The usual dose, varying according to the product used, the subject treated, and the affection concerned, can be from 100 mg to 1 gram per day in a normal human being when administered parenterally.

The invention also comprises a process of preparation of the product of formula I above and of its salts, the process including a novel sequence of steps.

This process is characterized in that the product of formula:

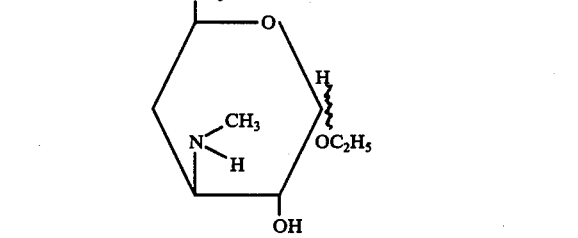

II is reacted with bromine or iodine (halogen) in the presence of an alkaline agent to obtain a product of the formula:

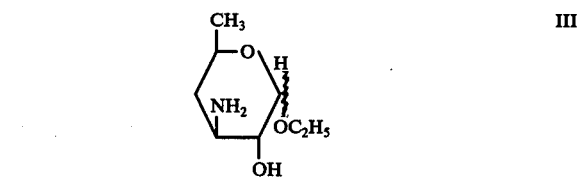

III which is then treated with ethyl chloroformate in the presence of an alkaline agent to obtain a product of the formula:

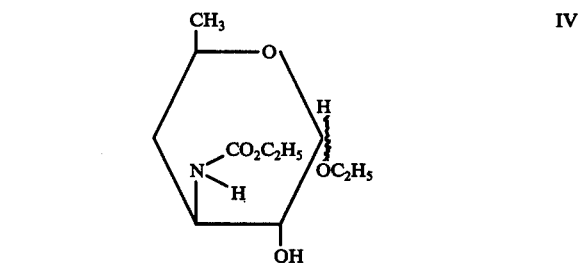

IV which is reacted with a benzyl halide in the presence of an alkaline agent to obtain the product:

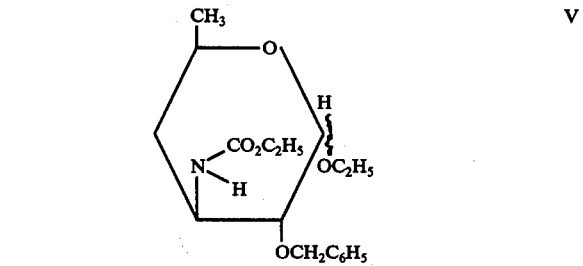

V which was treated with acetic anhydride in acetic acid in the presence of a strong acid to obtain the product having the formula:

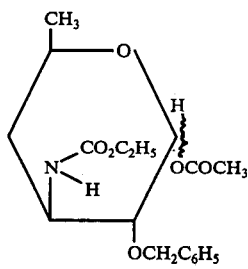  VI which was treated with anhydrous hydrochloric acid in the presence of acetyl chloride in an organic solvent to obtain a product of the formula:

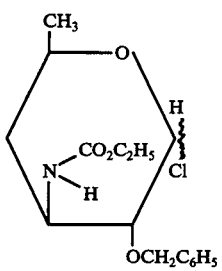  VII which was reacted with a product having the formula:

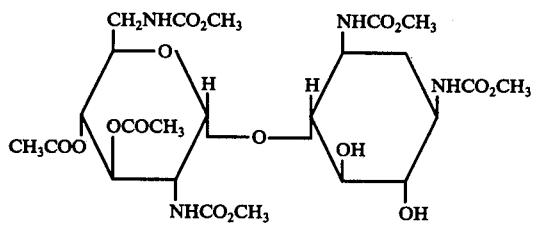  VIII in the presence of a catalyst to obtain a mixture of α and β anomers having the formulae:

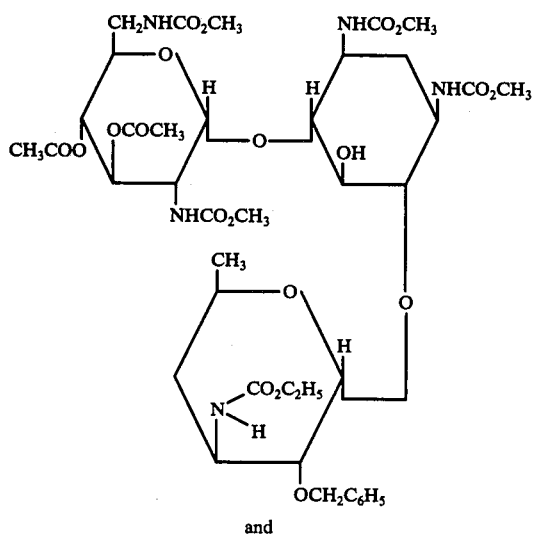  IX and

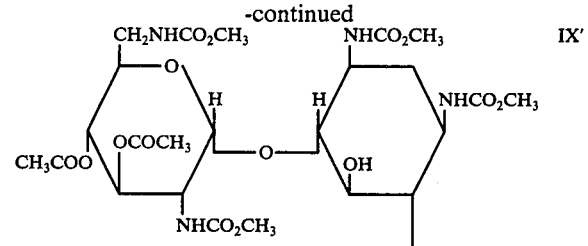  IX'

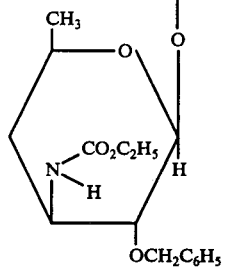

The mixture was treated with hydrogen in the presence of a catalyst and then with an alkaline base to obtain the product. The α anomer is separated from the mixture by conventional methods. If desired, the salts are formed by salification by the action of an organic or inorganic acid. The preferred operating conditions in the broad process described above are as follows:

The alkaline agent which is used during the reaction of bromine or iodine, i.e., halogen, on the product of formula II is preferably an alkaline alkoxide such as sodium methoxide, but other alkaline bases such as sodium hydroxide or potassium hydroxide or another alkaline alcoholate such as for example, sodium ethoxide, potassium ter-butylate or sodium ter-amylate may be used.

The alkaline agent which is used during the reaction of the ethyl chloroformate with the product of formula III is preferably sodium carbonate but other alkaline agents such as potassium carbonate, sodium bicarbonate, sodium hydroxide, potassium or lithium hydroxide or a tertiary organic base such as tertiary amine, for example, triethylamine or pyridine may be used.

The alkaline agent which is present during the reaction of the benzyl halide (e.g., benzylchloride or benzylbromide) with the product IV is particularly baryta (barium hydroxide) but sodium hydride, sodium amide or sodium hydroxide may be also used.

The strong acid which is present when acetic anhydride is reacted with the product of formula V is sulfuric acid, but other mineral acids such as hydrochloric acid, and organic acid such as trifluoroacetic acid, p-toluenesulfonic acid, a Lewis acid such as boron trifluoride, aluminium chloride or a sulfonic type ion exchange resin may be used.

The organic solvent present during the reaction of the anhydrous hydrochloric acid with the product of formula VI is preferably dioxane but other solvents such as ethyl ether, tetrahydrofuran or 1,2 dimethoxymethane may be used.

The reaction (condensation) between products VII and VIII is a named reaction referred to as KOENIGS - KNORR reaction, and is effected in the presence of a catalyst which is preferably mercuric cyanide. Although, one can also use other mercury salts, a silver or cadmium salt, or a tertiary amine, such as collidine.

As the hydrogenation catalyst to transform the mixture of products of formulae IX and IX' to a mixture of the reduced products, it is advantageous to use palladium deposited on carbon black, but one can also use other palladium or platinum salts, derivatives of platinum and other catalysts such as rhodium, ruthenium or nickel.

The alkaline agent which may be used to liberate the amine functions of the mixture of products is advantageously an aqueous solution of baryta (barium hydroxide) but other aqueous bases such as aqueous sodium or potassium hydroxide solutions may also be used.

The separation of the anomers of the resultant product is obtained by conventional physical procedures. The separation may preferably be obtained chromatographically using silica but alumina, cellulose or magnesium silicate can be used. The separation can also be obtained by using fractional crystallization or countercurrent separation techniques. Different pure or aqueous organic solvents or mixtures of solvents may be used to satisfactorily make the separation.

The acid salt of compounds of formula I may be formed by conventional techniques. Acids which may be used for this include for example, hydrochloric, hydrobromic, nitric, sulfuric, phosphoric, acetic, formic, benzoic, maleic, maleic, fumaric, succinic, tartaric, citric, oxalic, benzylic, glyoxylic, aspartic, alkane sulfonic, and arylsulfonic acids. The salification is preferably obtained in a solvent or a mixture of solvents such as water, ethers, such as ethyl ether, alcohols, such as ethanol or ketones, such as acetone.

The wavy line which connects the substituents on the carbon atom of the 1-position of the ring in formulae II, III, IV, V, VI and VII indicates that these substituents may be either α or β to the ring. These products exist in the α or β anomers or as a mixture thereof.

The product of formula VIII which is reacted with the product of formula VII is obtained according to a process which consists of reacting the product having the formula:

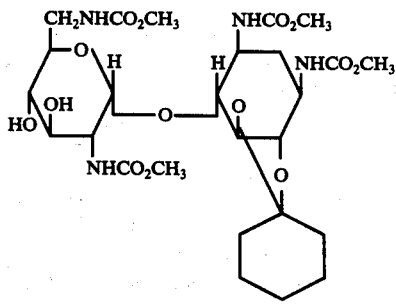

with acetic anhydride in the presence of an organic base to obtain a product of the formula:

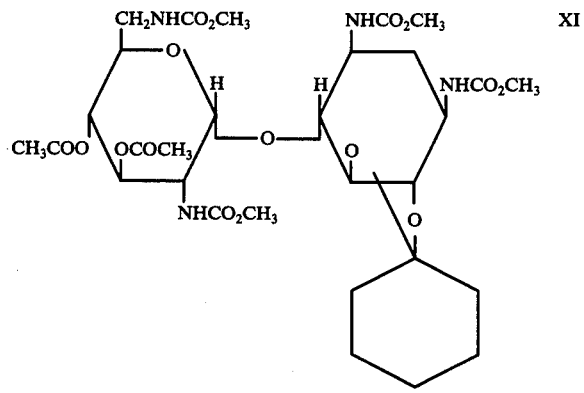

which is treated with an acidic agent to obtain the desired product of formula VIII.

The organic base used when acetic anhydride is reacted with the product of formula X is preferably pyridine but other organic bases such as lutidine or collidine may also be used.

The acid used to treat the product of formula XI is preferably aqueous acetic acid but other organic acids may be used such as oxalic or formic acid or aqueous mineral acids such as hydrochloric, sulfuric or the like.

Another object of the invention is the intermediate compound having the formula:

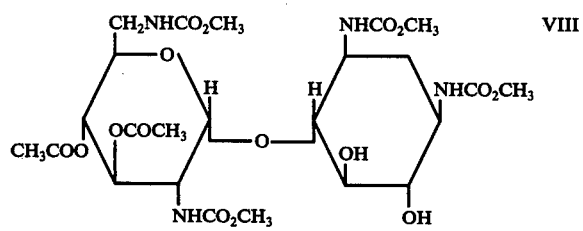

which is particularly useful as an intermediate in the preparation of the compound of formula I.

The following examples illustrate the invention without in any way being limiting thereon.

EXAMPLE 1

4-O-(2',6'-diamino 2',6'-didesoxy α,D-glucopyrannosyl) 6-O-(3"-amino 3",4",6"-tridesoxy α,D-xylohexopyrannosyl) 2-desoxy streptamine

Stage 1: ethyl 3-amino 3,4,6-tridesoxy D-xylohexopyrannoside 13.2 grams of ethyl 3-(N-methylamino) 3,4,6-tridesoxy D-xylohexopyronnoside (prepared according to the procedure described in the J. Org. Chem., 1965, 30, 1287) was dissolved in 500 ml of methanol containing 18.8 grams of sodium methylate. The solution is cooled to 5° C and then for 3 hours at room temperature. A 0.5 aqueous sodium thiosulfate solution containing 50 ml of ammonia is added until complete discoloration. The mixture is evaporated to dryness under vacuum, and the residue was dissolved in methylene chloride. The mineral salts are separated by filtration and evaporation of the solvent, the product thus obtained was purified by chromatography on silica eluted with a mixture of chloroform-isopropanol-ammonia (2:2:1). The product which still contains the product of the separation is again chromatographed on silica and eluted with a mixture of chloroform-methanol-triethylamine (90:5:5). 3.9 grams of ethyl 3-amino-3,4,6-tridesoxy -D-xylohexopyrannoside which was recrystallized from ethyl acetate to form crystals which sublimate at 150° C were obtained.

| Analysis: | $C_8H_{17}NO_3$ | | |
|---|---|---|---|
| Calculated: | C % 54.83 | H % 9.78 | N % 7.99 |
| Found: | 55.1 | 10.0 | 7.9 |

Stage 2: ethyl 3-(N-carbethoxyamino) 3,4,6-tridesoxy D-xylohexopyrannoside 3.89 grams of the product obtained from Stage 1 was dissolved in 30 mls of an aqueous solution of sodium carbonate and 2.5 ml of ethyl chloroformate was added thereto. This mixture was agitated for an hour and a half at room temperature (about 25° C) and then diluted with water and extracted with methylene chloride. After evaporation of the solvent 4.6 grams of ethyl 3-(N-carbethoxyamino) 3,4,6-tridesoxy D-xylohexopyrannoside were obtained; m-p 140° C.

Thin layer chromatography on silica:
Rf: 0.24 (benzene-ethyl acetate 1:1)

Stage 3: ethyl 2-O-benzyl 3-(N-carbethoxy amino) 3,4,6-tridesoxy D-xylohexopyrannoside 4.6 grams of the product obtained in the preceeding stage (Stage 2), 4.6 grams of anhydrous baryata, 2.3 grams of baryta (barium hydroxide) and 4.6 ml of benzyl bromide were dissolved in 15 ml of dimethylformamide. The mixture was agitated for sixty hours at ambient temperature (about 25° C) and 150 ml of water were added. The precipitated product is dried and then washed with water and dissolved in a mixture of methylene chloride and ethyl acetate. The organic phase is dried over sodium sulfate and the solvent evaporated. The obtained residue was chromatographed on silica using as an eluent a mixture of benzene-ethylacetate (8:2). 5.8 grams of ethyl 2-O-benzyl-3(N-carbethoxyamino) 3,4,6-tridesoxy D-xylohexopyrannoside melting at a temperature lower than 40° C were obtained.

Thin layer chromatography on silica:
Rf: (evidence of two anomers): 0.23–0.29 (benzene-ethylaceate 8:2).

Stage 4: 1-O-acetyl 2-O-benzyl 3-(N-carbethoxyamino) 3,4,6-tridesoxy D-xylohexopyrannose, anomers α and β.

22.3 grams of the product prepared in the preceding stage were dissolved in 220 ml of acetic acid containing 22 ml of acetic anhydride. 1.9 ml of concentrated sulfuric acid were added while the temperature was maintained at 20° C, followed by agitation for four hours at ambient temperature. The reaction mixture was then poured into water and extracted with ethyl acetate. The organic phase was washed with an aqueous sodium bicarbonate solution and water. The solvent was evaporated off and the residue was chromatographed on silica with a mixture of ether-hexane (1:1) as the eluant. The α anomer is first obtained.

Rf: 0.18 (silica, ether-hexane 1:1) then the β amoner m.p. 168° C.
Rf: 1.12 (silica: ether-hexane 1:1).

Stage 5: 4-O-(2',6'-di-(N-carbomethoxyamino) 2',6'-didesoxy 3',4'-di-O-acetyl α,D-glucopyrannosyl) 6-O-(3''-(N-carbethoxyamino) 2''-O-benzyl 3'',4'',6''-tridesoxy α,D-xylohexopyrannosyl) 1,3-di-N-carbomethoxy 2-desoxy streptamine 21 grams of the product obtained in the preceding stage were dissolved in 360 ml of dioxane containing 5% gaseous hydrochloric acid and 180 ml of acetyl chloride. The obtained solution was heated for an hour at 40° C and then evaporated to dryness under vacuum without allowing the temperature of the product to go above 40° C. The residue is dissolved in 100 ml of dioxane and the thus obtained solution was added to, at 60° C, a solution of 12 grams of 3',4'-di-O-acetyl tetra-N-carbomethoxy neamine in 200 ml of dioxane which also contained 12 grams of mercuric cyanide. The mixture was allowed to stand for 16 hours and then the reaction mixture was cooled and poured into an aqueous solution of sodium bicarbonate. The product was extracted from this solution with methylene chloride. The methylene chloride extract was evaporated to dryness under vacuum to obtain the product. The resulting residue was chromatographed on silica using as an eluant a mixture of chloroform-acetone (7:3). About 9.2 grams of the product was obtained as a mixture of α and β anomers.

Thin layer chromatography gave:
Rf: 0.23 (silica:chloroform-acetone 7:3).

Stage 6: 4-O-(2',6'-diamino 2',6'-didesoxy α,D-glucopyrannoxyl) 6-O-(3''-amino 3'',4'',6''-tridesoxy α,D-xylohexopyrannoxyl) 2-desoxy streptamine 9.2 grams of the product obtained in the preceding stage was dissolved in a mixture of 150 ml ethanol, 75 ml methylene chloride, and 7 ml of 2N hydrochloric acid. 6.5 grams of 10% palladium on carbon black was added. The mixture was agitated in a hydrogen atmosphere. After three hours the mixture is cooled and the catalyst separated by filtration. The filtrate is made alkaline with a basic quaternary ammonium ion exchange resin. The resin is separated and the solution was dried under vacuum.

A white solid was obtained which was dissolved in 80 ml of water to which was added 80 grams of baryta (barium hydroxide). This was heated to 90° C during four hours, cooled and brought to a pH of 2 with a solution of normal sulfuric acid. The mixture is filtered and the filtrate made alkaline with a basic quaternary ammonium ion exchange resin. The resin was separated and the filtrate was evaporated to dryness under vacuum.

An amorphous product was obtained which was purified by passing through a column of carboxylic type ion eschange resin in the ammonium form using as an eluent 0.1 and 0.2 N ammonia. The product obtained was chromatographed on silica using a mixture of chloroform-methanol-ammonia (2:2:1).

250 mg of the β anomer and 870 mg of the α anomer of 4-O-(2',6'-diamino 2',6', didesoxy α,D-glucopyrannosyl) 6-O-(3''-amino-3'',4'',6''-tridesoxy α,D-xylohexopyrannosyl) 2-desoxy streptamine were obtained.

Anomer α: $[\alpha]D^{20} = 115°$ (C=0.5%, water)
Rf: 0.30 (silica, chloroform-methanol-ammonia 2:2:1).
Anomer β: Rf: 0.38 (silica, chloroform-methanol-ammonia 2:2:1)

The 3′,4′ di-O-acetyl tetra-N-carbomethoxy neamine used in Stage 5 was prepared as in the following example.

Stage 1: 5,6-O-cyclohexylidene 3′,4′di-O-acetyl tetra-N-carbomethoxy neamine 38 grams of 5,6-O-cyclohexylidene tetra-N-carbomethoxy neamine (prepared according to the procedure in the Journal of Antibiotics, 1971, page 711) was dissolved in a mixture comprising 240 ml of pyridine and 80 ml of acetic anhydride. The mixture was allowed to stand at ambient (room) temperature for twenty hours and then the reaction mixture was evaporated to dryness under vacuum. The residue was purified by chromatography on silica using a mixture of chloroform-acetone (8:2) as the eluant.

32 grams of 5,6-O-cyclohexylidene 3′,4′-di-O-acetyl tetra-N-carbomethoxy neamine were obtained.

Thin layer chromatography.
Rf: 0.31 (silica, chloroform-acetone 7:3).

Stage 2: 3′,4′-di-O-acetyl tetra-N-carbomethoxy neamine 31 grams of the product of the preceding stage was dissolved in 240 ml of acetic acid contaiing 60 ml of water. The mixture was heated to 60° C during four hours under agitation. The mixture is then evaporated to dryness under vacuum and 27.5 grams of 3′,4′-di-O-acetyl tetra-N-carbomethoxy neamine in the form of a colorless solid were obtained.

Thin layer chromatography.
Rf: 0.31 (silica, chloroform-methanol 9:1).

EXAMPLE 2

An injection preparation is prepared as follows:
Product described in Example 1    50 mg
Sterile aqueous excipient         1 ml Pharmacological study of the product described in Example 1.

The antibacterial activity has been measured in vitro by the method of dilution in liquid.

A series of tubes is prepared in which is distributed the same quantity of nutritive medium. Increasing quantities of the antibiotic under study are distributed, then each tube is inoculated with a bacterial strain. After a 24, 48 and 72 hour incubation in a 37° C oven, inhibition of the bacterial growth is appraised by transillumination which determines the minimal inhibiting concentrations (CMI) of the products expressed as $\mu g/cm^3$. The product described in Example 1 gave the results shown in the following table:

| STRAINS | CMI in $\mu g/cm^3$ | | |
|---|---|---|---|
| | 24 h | 48 h | 72 h |
| *Staphylococcus* Oxford U.C. 1061 Penicillino-sensible | 0.2 | 0.2 | 0.2 |
| *Staphylococcus aureus* U.C. 1128 Penicillino-resistant | 0.2 | 0.2 | 0.5 |
| *Streptococcus Hemolyticus* 905 | 20 | 20 | 20 |
| *Streptococcus faecalis* 5432 | >100 | | |
| *Bacillus subtilis* | ≦0.05 | ≦0.05 | ≦0.05 |
| *Escherichia Coli* U.C. 1020 | 1 | 1 | 1 |
| *Pseudomonas pyocyanea* | >100 | | |
| *Klebsiella pneumoniae* 52145 | 0.2 | 0.5 | 0.5 |
| *Proteus mirabilis* A.235 | 2 | 2 | 2 |

These results illustrate the good antibiotic activity of the product.

What is claimed is:

1. The 4-O-(2′,6′diamino 2′,6′-didesoxyα, D-glucopyrannosyl) 6-O-(3″-amino 3″,4″,6″-tridesoxy α, D-xylohexopyrranoxyl) 2-desoxy streptamine of the formula:

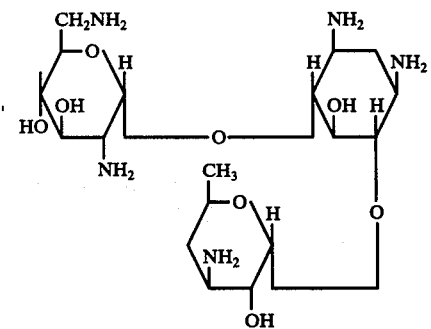

or the pharmaceutically acceptable salts with mineral or organic acids thereof.

2. A product according to claim 1 wherein the mineral or organic acid is sulfuric acid, hydrochloric acid, phosphoric acid, hydrobromic acid, nitric acid, succinic acid, tartaric acid, formic acid, acetic acid, citric acid, oxalic acid, benzylic acid, glyoxylic acid, aspartic acid, benzoic acid, para-toluenesulfonic acid, fumaric acid, maleic acid or methanesulfonic acid.

3. A process for the preparation of the product of claim 1 which comprises reacting a compound of the formula:

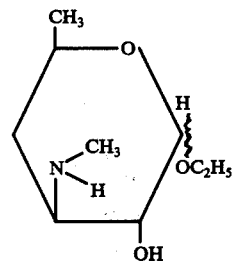

with bromine or iodine in the presence of an alkaline agent selected from the group consisting of alkaline hydroxide and alkaline alcoholate to obtain a product of the formula:

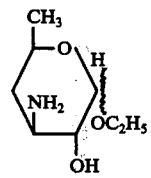

treating said product with ethyl chloroformate in the presence of an alkaline agent selected from the group consisting of sodium carbonate, potassium carbonate, sodium bicarbonate, sodium hydroxide, potassium hydroxide, lithium hydroxide and tertiary amines to obtain a product of the formula:

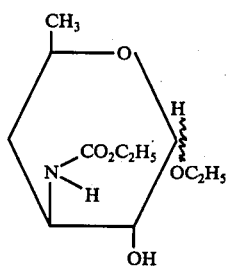

which is reacted with a benzyl halide in the presence of an alkaline agent selected from the group consisting of baryta, sodium hydride, sodium amide and sodium hydroxide to obtain the product of the formula:

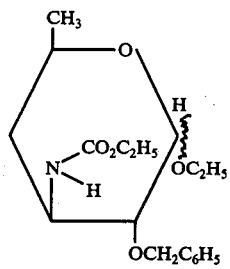

which is treated with acetic anhydride in acetic acid in the presence of a strong acid selected from the group consisting of mineral acids, organic acids, Lewis acids and sulfonic type ion exchange resins to obtain the product having the formula:

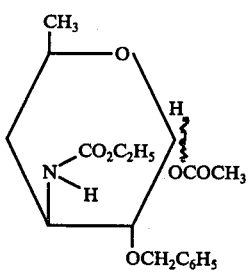

which is then treated with anhydrous hydrochloric acid in the presence of acetyl chloride in an organic solvent to obtain a product of the formula:

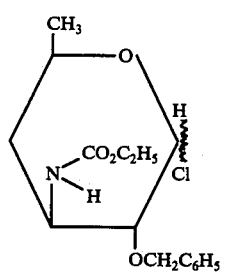

which is reacted with a product having the formula:

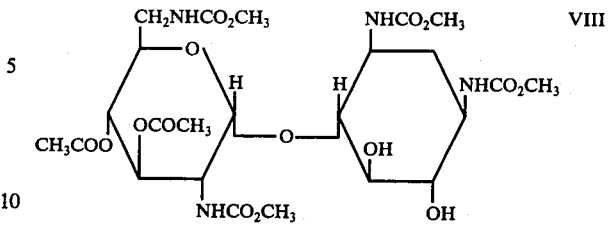

in the presence of a catalyst to obtain a mixture of α and β anomers having the formula:

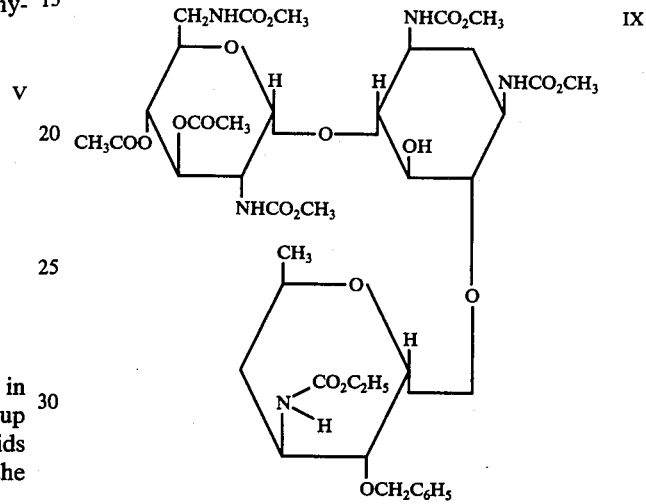

and

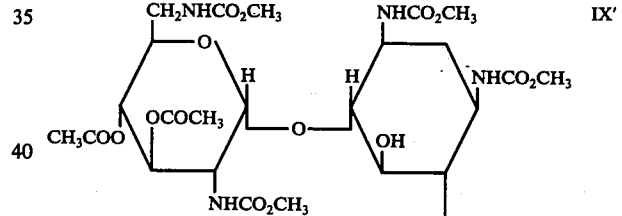

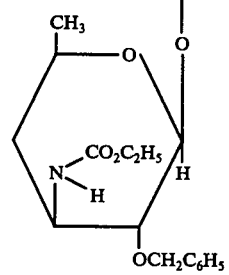

the said mixture being reduced with hydrogen in the presence of a catalyst and then treated with an alkaline base selected from the group consisting of baryta, sodium hydroxide and potassium hydroxide, the product of formula I being separated from the mixture of anomers thus obtained.

* * * * *